(12) United States Patent
Sugaya et al.

(10) Patent No.: US 8,772,032 B2
(45) Date of Patent: Jul. 8, 2014

(54) METHODS AND MATERIALS FOR STIMULATING PROLIFERATION OF STEM CELLS

(75) Inventors: Kiminohu Sugaya, Winter Park, FL (US); Sudipta Seal, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/044,770

(22) Filed: Mar. 10, 2011

(65) Prior Publication Data

US 2011/0159056 A1 Jun. 30, 2011

Related U.S. Application Data

(62) Division of application No. 11/968,393, filed on Jan. 2, 2008, now abandoned.

(60) Provisional application No. 60/883,081, filed on Jan. 2, 2007.

(51) Int. Cl.
*C12N 5/00* (2006.01)
*A01N 59/16* (2006.01)
*A01N 63/00* (2006.01)

(52) U.S. Cl.
USPC .......................... 435/395; 435/325; 424/617

(58) Field of Classification Search
USPC .................. 435/395, 325; 424/617
See application file for complete search history.

(56) References Cited

U.S. PATENT DOCUMENTS

| | | | |
|---|---|---|---|
| 5,486,359 A * | 1/1996 | Caplan et al. | 424/93.7 |
| 7,347,987 B2 | 3/2008 | McGinnis et al. | |
| 7,534,453 B1 | 5/2009 | Rzigalinski et al. | |
| 7,888,119 B2 * | 2/2011 | Sugaya et al. | 435/395 |
| 2003/0139410 A1 | 7/2003 | Sugaya | |
| 2005/0031517 A1 | 2/2005 | Chan | |
| 2006/0110440 A1 | 5/2006 | Sugaya | |
| 2006/0134789 A1 | 6/2006 | Sugaya | |
| 2006/0137567 A1 | 6/2006 | Yadav | |
| 2006/0269760 A1 | 11/2006 | Sugama | |
| 2006/0280729 A1 | 12/2006 | Mistry | |
| 2007/0243175 A1 | 10/2007 | Phillips et al. | |

FOREIGN PATENT DOCUMENTS

| | | |
|---|---|---|
| WO | WO2006118954 | 11/2006 |
| WO | WO2007/002662 | 1/2007 |
| WO | WO2008064357 | 5/2008 |

OTHER PUBLICATIONS

Brunner et al. In vitro cytotoxicity of oxide nanoparticles: Comparison to asbestos, silica, and the effect of particle solubility. environ. Sci. Technol. 40:4374-4381, 2006.*

Rzigalinski et al. Cerium oxide nanoparticles increase the lifespan of cultured brain cells and protect against free radical and mechanical trauma. FASEB Journal 17(4-5), Abstract No. 3377.24 Mar. 2003 p. A606.

Niu, J. et al. Cardiovascular effects of cerium oxide nanoparticles in a transgenic murine model of cardiomyopathy. Cardiovas. Res. Nov. 30, 2006, Nov. 2006, vol. 73, No. 3, pp. 549-559.

Qureshi, M. A. et al. Increased Exhaled nitric oxide following autologous peripheral hematopoietic stem cell transplantation; a potential marker of idiopathic pneumonia syndrome. Chest Jan. 2004, vol. 125, No. 1, pp. 281-287; Abstract; pp. 72 P7f.

* cited by examiner

*Primary Examiner* — Quang Nguyen
(74) *Attorney, Agent, or Firm* — Timothy H. Van Dyke; Beusse, Wolter, Sanks & Maire, P.A.

(57) ABSTRACT

Disclosed herein are methods and materials for influencing proliferation of stem cells. Specifically exemplified herein are compositions comprising cerium oxide nanoparticles which can be used to stimulate proliferation of stem cells under common culture conditions, or which can be utilized to improve therapeutic outcomes.

2 Claims, No Drawings

METHODS AND MATERIALS FOR STIMULATING PROLIFERATION OF STEM CELLS

RELATED APPLICATIONS

This is a division of U.S. Ser. No. 11/968,393, filed Jan. 2, 2008 now abandoned, and also claims priority to U.S. Ser. No. 60/883,081, filed Jan. 2, 2007, which is incorporated herein by reference in its entirely.

BACKGROUND OF THE INVENTION

Patients currently suffering from neurodegenerative conditions such as Alzheimer's and Parkinson's have limited treatment options. Conventional drug therapy helps delay or reduce the symptoms of disease but is unable to restore complete functionality of the brain or repair damaged tissue. Through stem cell-based therapies, scientists aim to transplant cells in order to regenerate damaged tissue and restore proper function. In addition to addressing neurodegenerative diseases, stem cell based therapies show much promise in addressing a vast number of other diseases, injuries and conditions. The discovery of safe and inexpensive compositions to modulate stem cell proliferation would be a beneficial advancement in the filed of stem cell-based therapies and basic research.

DETAILED DESCRIPTION

Scientists are beginning to realize the potential power of stem-cell based therapies. It is widely recognized that stem cell transplantation may lead to treatments and/or cures of baneful disease states, degeneration and/or injury. The ability to stimulate the proliferation of stem cells in vivo or in vitro will be of tremendous benefit. The subject invention is based on the inventors discovery that certain nanoparticles can affect the proliferation of stem cells.

In one embodiment, the subject invention pertains to a method of improving therapeutic outcomes of implanted stem cells comprising administering a Cerium Oxide ($CeO_2$) nanoparticle composition in conjunction with stem cell implantation. The administration of the Cerium Oxide composition can be at or proximate to a target stem cell implantation site in a human or nonhuman animal. In an alternative embodiment, the environment may be further modified by provision of influencing factors or by cleaning the environment of undesired or toxic agents that may affect administered stem cells in an undesired way. The administered stem cells may be unmodified or may themselves be engineered to be biased toward a target differentiation endpoint. U.S. Patent Publication Nos. 20060134789 and 20060110440 are incorporated by reference to provide examples of stem cells engineered for negative and positive differentiation biasing that are contemplated for use with the methods taught herein.

In another embodiment, the subject invention involves the administration of a composition comprising a administering Cerium Oxide nanoparticle composition to a body and administering stem cells to said body. The composition is administered at a locus in said body so as to allow contact with the stem cells. This may be at the same location, proximate to the location or distal to the location of where stem cells are administered.

Stem cells may be administered by injecting one or a plurality of stem cells with a syringe, inserting the stem cells with a catheter or surgically implanting the stem cells. In certain embodiments, the stem cells are administered into a body cavity fluidly connected to a target tissue. In certain preferred embodiments, the body cavity is a brain ventricle. In other embodiments, the stem cells are inserted using a syringe or catheter, or surgically implanted directly at the target tissue site. In other embodiments, the stem cells are administered parenterally. Parenteral administration is historically defined as administration via a route that bypasses the gastrointestinal tract. Therefore, technically parenteral administration includes intraventricular administration, but intraventricular administration is typically discussed herein as separate from other modes of administration that may fall under 'parenteral administration'.

The compositions can be administered alone or in combination with at least one other agent, such as stabilizing or buffer compounds, which can be administered in any sterile, biocompatible pharmaceutical carrier, including, but not limited to, saline, buffered saline, dextrose, and water. In addition to the critical components of compositions discussed herein, cells or influencing factors, the compositions can contain suitable pharmaceutically acceptable carriers comprising excipients and auxiliaries which facilitate processing of the active compounds into preparations which can be used pharmaceutically. Generally compositions can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Factors can be administered at the same location as administered stem cells. Administration of influencing factors and stem cells can be conducted simultaneously, or one prior to the other, and at the same or different locations so long as the relative locations allow for the factors to influence the stem cells.

The administration of cerium oxide nanoparticles to stem cells can be conducted in vivo, ex vivo, in situ, and/or in vitro. According to a specific embodiment, cerium oxide nanoparticles are applied to stem cells in vitro. This will aid and facilitate basic experiments conducted on stem cells that will benefit from stimulation of the stem cells or to create for the stem cells an environment where oxidants are minimized. In other embodiments, the invention is directed to the stem cell proliferating cerium oxide nanoparticle compositions themselves.

In other embodiments, the environment of administered stem cells is modified by administration of a separate population of stem cells that are engineered to express influencing factors. Engineered stem cells designed to express influencing factors may be produced according to previously disclosed methods. See for example U.S. Patent Publication Nos. 20060134789 and 20060110440. According to a specific method embodiment, a population of therapeutic stem cells are administered to a locus of a subject's body and a population of engineered stem cells is administered at or proximate to the therapeutic population. Influencing factors are expressed and released from the engineered stem cells which in turn influence the therapeutic stem cells for a desired objective.

Thus, the invention also provides improved methods of treating health conditions implementing a stem cell strategy. For example, the methods taught herein may be used to treat or ameliorate symptoms due to a corporal or neurological (affecting nervous system), such as a deficit caused by a neurodegenerative disease, a traumatic injury, a neurotoxic injury, ischemia, a developmental disorder, a disorder affecting vision, an injury or disease of the spinal cord, a demyelinating disease, an autoimmune disease, an infection, an inflammatory disease, or corporal disease, disorder, injury, trauma, malfunction, degeneration or loss. See, for example, U.S. Patent Publication No. 20030139410. In preferred embodiments, implanted stem cells are capable of proliferating, migrating to an area of tissue damage, and/or differentiating in a tissue-specific manner and functioning in a manner that reduces the neurological or corporal deficit. Stem cells may be administered by injection with a syringe, inserting cells with a catheter or surgically implanting cells. In certain embodiments, stem cells are injected with a syringe into a body cavity that is fluidly-connected to the area of neurological or corporal deficit. In certain preferred embodiments, the body cavity is a brain ventricle. In other embodiments, stem cells are inserted with a catheter into a body cavity that is fluidly-connected to the area of neurological or corporal deficit. In certain preferred embodiments, the body cavity is a brain ventricle. In still further additional embodiments, stem cells are surgically implanted into a body cavity that is fluidly-connected to the area of neurological or corporal deficit. In certain preferred embodiments, the body cavity is a brain ventricle. Stem cells can also alternatively be inserted using a syringe or catheter or surgically implanted directly at the site of the neurological or corporal deficit or systemically (e.g., intravenously).

The invention provides methods of delivery and transplantation of stem cells to ameliorate the effects of age, physical and biological trauma and degenerative disease on the brain or central nervous system of a human or nonhuman animal, as well as other tissues such as, for example, retinal tissue. It is well recognized in the art that transplantation of tissue into the CNS offers the potential for treatment of neurodegenerative disorders and CNS damage due to injury. Transplantation of new cells into the damaged CNS has the potential to repair damaged circuitries and provide neurotransmitters thereby restoring neurological function. It is also recognized in the art that transplantation into other tissue, such as eye tissue, offers the potential for treatment of degenerative disorders and tissue damage due to injury. As disclosed herein, the invention provides methods for methods of modifying a tissue environment to influence proliferation, migration and differentiation of administered stem cells when introduced into a target site. In a certain specific embodiments, target sites may be those appropriate for treatment of neurological disorders and CNS damage.

Recipients of administered stem cells can be immunosuppressed, either through the use of immunosuppressive drugs such as cyclosporin, or through local immunosuppression strategies employing locally applied immunosuppressants, but such immunosuppression need not necessarily be a prerequisite in certain immunoprivileged tissues such as, for example, brain and eye tissues. In certain embodiments, the delivery method of the invention can cause less localized tissue damage to the site of cell damage or malfunction than existing methods of delivery.

In certain embodiments, administered stem cells are autologous in nature, i.e., prepared from the recipient's own tissue. In such instances, the progeny of stem cells can be generated from dissociated or isolated tissue and proliferated in vitro using known methods. In the case of mesenchymal stem cells (MeSCs), progeny can be generated from MeSCs isolated from, for example, bone marrow. Upon suitable expansion of cell numbers, the stem cells of the invention can be harvested and readied for administration into the recipient's affected tissue.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

EXAMPLE 1

Preparation of Cerium Oxide Nanoparticles

Cerium oxide nanoparticles of a size approximately 2 nm to approximately 10 nm in diameter, are prepared by a process including the steps of dissolving approximately 0.5 grams to approximately 1.0 grams of $Ce(NO_3)_3.6H_2O$ in deionized water to make approximately 10 mls of solution to form a first solution, followed by dissolving approximately 3 grams to approximately 4 grams of AOT (surfactant) in approximately 200 ml of solvent to form a second solution, followed by combining the first and the second solutions, followed by stirring the combined solutions for approximately 30 minutes, and drop wise adding approximately 30% hydrogen peroxide ($H_2O_2$) until the stirred combined solution becomes yellow, and subsequently stirring for approximately 30 minutes to approximately 60 minutes more. Thus, aqueous reverse micelles (RMs) are surfactant aggregates in nonpolar solvents that enclose packets of aqueous solution in their interior. The size of the water droplet can be tuned by varying the ratio of water to surfactant. RMs used as reaction media in the production of nanoparticles whose size and shape are controlled by water and surfactant ratio. The surfactant is stripped off using simple washing and drying. Size: 3-5 nm.

EXAMPLE 2

The synthesis of ceria was carried out by direct synthesis route from the cerium precursor ($Ce(NO_3)_3.6H_2O$) dissolved in water. Oxidation of cerium nitrate was carried out using hydrogen peroxide ($H_2O_2$). It is a very simple one step process yielding ceria nanoparticles dispersed in water (a very useful delivery media for biological studies). The process leads to formation of cerium oxide nanoparticles of 15-20 nm particle size (agglomerates) consisting 3-5 nm spherical crystals.

EXAMPLE 3

Particles may be obtained via heating of the particles in produced in Example 1 above, anywhere between 100-400 C.

EXAMPLE 4

Cerium oxide particles are obtained from commercially available sources. Particles are dried from the slurry, washed in water and redispersed in the water at a certain pH. Without being bound to any particular theory, it is believed that the variation in the stem cell proliferation, though not yet shown to be statistically significant, appears to be attributable to difference in the Ce+3/Ce+4 ratio in the samples.

EXAMPLE 5

Stimulation of Stem Cell Proliferation

Stem cell growth and division rates can be increased by lowering the oxidative stress on the cells. We propose using this method to increase the proliferation rates of stem cells under common culture conditions. Specifically, we can improve stem cell proliferation rates by as much as 50%. Furthermore, we propose that this method can be used to enable the growth of stem cells for emergency tissue repair as well as for therapeutic use. This therapy can be used in conjunction with currently available drugs and biologics with little concern over negative interactions and helps eliminate the possibility for graft-verse-host disease. Using five different samples of cerium oxide, CeO2, nanoparticles, size and shape, 3-5 nm spherical, 11-15 nm agglomerates of 3-5 nm individual crystals, 10-20 nm spherical, 7-10 nm spherical, and 10-20 nm cuboidal, the inventors found a good working concentration by making serial dilutions of each sample, then applied each for a plated dish of rat mesenchymal stem cells, also known as adult stem cells. Although a wide range of concentrations can be used, the inventors found that 10 nM appeared to be an optimal concentration. When rat and human mesenchymal stem cells were plated at known densities, treated with one of the CeO2 samples, allowed to grow for periods of 24, 48, and 72 hours, then performed a cell count for each of the samples and the control untreated cells, the rate of cell proliferation had a marked increase. Though all samples showed an influence on proliferation, Sample 3, which is composed of CeO2 nanoparticles 10-20 nm in size and spherically shaped and showed highest increase, increased mesenchymal stem cell proliferation rates by as much as 50%.

While a number of embodiments of the present invention have been shown and described herein in the present context, such embodiments are provided by way of example only, and not of limitation. Numerous variations, changes and substitutions will occur to those of skilled in the art without materially departing from the invention herein. It should be borne in mind that all patents, patent applications, patent publications, technical publications, scientific publications, and other references referenced herein are hereby incorporated by reference in this application, in their entirety to the extent not inconsistent with the teachings herein.

What is claimed is:

1. A method of stimulating proliferation of a population of stem cells, said method comprising contacting said population with cerium oxide nanoparticles in vitro, wherein said nanoparticles are spherical in shape and are about 10-20 nm in size and are provided in a culture media at a concentration to promote proliferation of said stem cells; and culturing said population of stem cells in said culture media under conditions and time period to increase the population of stem cells.

2. The method of claim 1, wherein said stem cells are mesenchymal stem cells.

* * * * *